US006387695B1

(12) United States Patent
Evans et al.

(10) Patent No.: US 6,387,695 B1
(45) Date of Patent: May 14, 2002

(54) DNA PHARMACEUTICAL FORMULATIONS COMPRISING CITRATE OR TRIETHANOLAMINE AND COMBINATIONS THEREOF

(75) Inventors: Robert K. Evans, Souderton; David B. Volkin, Doylestown; Mark W. Bruner, Norristown; Zheng Xu, Blue Bell, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/218,590

(22) Filed: Dec. 22, 1998

Related U.S. Application Data

(60) Provisional application No. 60/068,721, filed on Dec. 23, 1997.

(51) Int. Cl.[7] .............................................. C12N 15/88
(52) U.S. Cl. ................... 435/320.1; 435/69.1; 435/325; 435/455
(58) Field of Search ............................ 435/325, 69.1, 435/320.1, 455; 514/44; 424/93.21

(56) References Cited

U.S. PATENT DOCUMENTS

| | | | | |
|---|---|---|---|---|
| 4,840,892 A | * | 6/1989 | Adams et al. .................. | 435/5 |
| 5,211,960 A | | 5/1993 | Babior | |
| 5,260,433 A | * | 11/1993 | Engelhardt .................. | 536/23.1 |
| 5,683,866 A | * | 11/1997 | Sarkar et al. .................... | 435/5 |
| 5,976,567 A | * | 11/1999 | Wheeler et al. ............ | 424/450 |
| 5,994,136 A | * | 11/1999 | Lollo et al. .................... | 514/44 |

FOREIGN PATENT DOCUMENTS

| | | |
|---|---|---|
| WO | WO97/40839 | 11/1997 |

OTHER PUBLICATIONS

Lahiri et al. (Current Science, vol. 59, No. 23, pp. 1254–1255), 1990.*
Berge et al. (J. Pharmaceutical Sciences, vol. 66, No. 1, pp. 1–19), 1977.*
Krugel et al., Transfection of Protoplasts from Streptomyces lividans 66 with Actinophage SH10 DNA, Mol. gen. Genet, vol. 177, pp. 297–300, 1980.*
Ohse et al., Effect of Plasmid DNA Sizes and Several Other Factors on Transformation of Bacillus subtilis ISW1214 with Plasmid DNA by Electroporation, Biosci. Biotech. Biochem., vol. 59, 1995, p. 1995.*
Nunomura et al. 'Effect of Various Anions on the Stepwise Melting of Plasmid DNA',J. Gen Appl. Microbiol. vol. 39, pp 259–605, 1993.

* cited by examiner

*Primary Examiner*—Dave T. Nguyen
(74) *Attorney, Agent, or Firm*—J. Mark Hand; Jack L. Tribble

(57) ABSTRACT

The present invention relates to nucleic acid formulations of pharmaceutical products which comprise citrate and/or triethanolamine in concentrations which enhance stability of the nucleic acid. These formulations are suited for situations where prolonged storage occurs during the distribution and/or storage period prior to use.

20 Claims, 3 Drawing Sheets

DNA PHARMACEUTICAL FORMULATIONS COMPRISING CITRATE OR TRIETHANOLAMINE AND COMBINATIONS THEREOF

CROSS-REFERENCE TO RELATED APPLICATIONS

This application claims the benefit under 35 U.S.C. §119 (e) of U.S. Provisional Application Serial No. 60/068,721, filed Dec. 23, 1997.

STATEMENT REGARDING FEDERALLY-SPONSORED R&D

Not applicable.

REFERENCE TO MICROFICHE APPENDIX

Not applicable.

FIELD OF THE INVENTION

The present invention relates to formulations of nucleic acid pharmaceutical products, specifically formulations of nucleic acid vaccine products and nucleic acid gene therapy products which comprise citrate and/or triethanolamine at pharmaceutically effective concentrations. DNA stability is increased in the pharmaceutical formulations of the present invention, allowing for long term storage and ease of distribution of DNA-based pharmaceutical products.

BACKGROUND OF THE INVENTION

DNA plasmid vaccines undergo a physiochemical change from supercoiled to the open circular and linear form during storage as a pharmaceutical entity. A variety of storage conditions such as low pH, high temperature and low ionic strength can accelerate this deleterious process.

The nucleic acid component of the formulations disclosed within this specification are free of nuclease activity, leaving the chain scission reaction as the sole known cause in converting supercoiled plasmid to the open circular and linear forms. The chain scission reaction takes on two distinct chemical mechanisms: (1) depurination followed by β-elimination and/or (2) free radical oxidation. Previous attempts to overcome these chemical-induced destabilizing mechanisms have included lyophilizing formulations containing DNA or by adding combinations of free radical scavengers and metal ion chelators to an aqueous formulation. In WO97/40839, the combination of EDTA and ethanol has been reported to be an effective inhibitor of free radical oxidation of DNA. However, this formulation requires the addition of two separate components to enhance stability. More importantly, the combination of EDTA and ethanol significantly increases the osmolarity of the formulation while the inclusion of EDTA in vaccine formulations has not of yet received worldwide acceptability. WO97/40839 also discloses various DNA vaccine formulations, but does not teach or suggest the use of citrate and/or triethanolamine to enhance DNA stability.

It would be useful to identify pharmaceutical formulations comprising a physiologically advantageous pH and osmolality which enhance DNA vaccine stability over longer periods of time at ambient temperatures. The present invention addresses and meets these needs by disclosing the ability to enhance stability of such formulations by the addition of citrate and/or triethanolamine at pharmaceutically acceptable concentrations.

SUMMARY OF THE INVENTION

The present invention relates to nucleic acid formulations of pharmaceutical products, especially nucleic acid formulations for use as nucleic acid vaccine products and nucleic acid gene therapy products. The formulations of the present invention stabilize the conformation of nucleic acids in pharmaceutical products. It will be evident upon review of this specification that the preferred template for stabilization is plasmid DNA. However, the formulations of the present invention may also be used to enhance stability of other nucleic acid molecules which are a part of a pharmaceutical formulation, including but not limited to other DNA forms such as genomic DNA molecules, complementary DNA (cDNA) molecules, which may be single (coding or non-coding strand) or double stranded, as well as synthetic DNA, such as a synthesized, single stranded polynucleotide. Additionally, nucleic acid pharmaceutical formulations of the present invention may also be used to enhance stability of other ribonucleic acid molecules (RNA), including but not limited to RNA-based vaccines, RNA-based gene therapy products, isolated messenger RNA (mRNA), isolated transfer RNA (tRNA) and synthetic RNA oligonucleotides.

The present invention relates to a nucleic acid pharmaceutical formulation which comprises citrate at a concentration which results in an increase in stability of the nucleic acid entity. It will be well within the purview of the skilled artisan to use the teachings of this specification to generate various nucleic acid formulations which contain citrate and which in turn, due to the presence of citrate, result in increased nucleic acid stability. To this end, it will be known that variations in formulation composition may include, but are not limited to, variations in pH within an acceptable range for storage of a biologically active nucleic acid template, preferably in a range from about 7.0 to about 9.5; variations in the buffers utilized, including but not limited to Tris, glycine, sodium phosphate, potassium phosphate, lithium phosphate, sodium bicarbonate, potassium bicarbonate, lithium bicarbonate, sodium borate, potassium borate, lithium borate and sodium, potassium or lithium citrate; variations in salt concentration; and addition of sugars including but not limited to 6-carbon polyhydric alcohols such as sorbitol, mannitol and dulcitol and/or disaccharides such as sucrose, lactose, maltose or trehalose, as well as various adjuvants which may stimulate the intended in vivo application. It will be evident to one of ordinary skill in the art that a formulation of the present invention will have a tonicity that is acceptable for parenteral injection.

One embodiment of the present invention relates to a nucleic acid formulation comprising a nucleic acid molecule, a pharmaceutically acceptable buffer to adjust the pH from about 7.0 to about 9.5, and citrate or a pharmaceutically acceptable salt thereof, including but not limited to sodium, potassium, lithium and triethanolamine salts.

Another embodiment of the present invention relates to a nucleic acid formulation wherein the nucleic acid template is a plasmid DNA construct and which comprises a pharmaceutically acceptable buffer at a pH from about 7.0 to about 9.5, and citrate or a pharmaceutically acceptable salt thereof, including but not limited to sodium, potassium, lithium and triethanolamine salts.

Another embodiment of the present invention relates to a nucleic acid formulation wherein the nucleic acid template is a plasmid DNA construct and which comprises a pharmaceutically acceptable buffer at a pH from about 7.7 to about 8.5, and citrate or a pharmaceutically acceptable salt thereof, including but not limited to sodium, potassium, lithium and triethanolamine salts.

An additional embodiment of the present invention relates to a nucleic acid formulation wherein citrate is a component of the formulation as well as a DNA plasmid template and phosphate buffered saline (PBS, contains 150 mM NaCl unless specified otherwise) wherein the pH is adjusted from about pH 7.2 to about pH 8.0 and the NaCl concentration is present in a range up to about 150 mM.

Yet another embodiment of the present invention relates to a nucleic acid formulation wherein citrate is a component of the formulation as well as a DNA plasmid template and 10 mM phosphate buffered saline, pH 7.7.

A preferred embodiment of the present invention relates to a nucleic acid formulation wherein citrate is present at about 100 mM in 10 mM phosphate buffer or is present from about 1 mM to about 20 mM in 10 mM phosphate buffered saline at pH 7.7.

An especially preferred embodiment of the present invention relates to a nucleic acid formulation wherein the DNA plasmid of interest is present in 10 mM citrate and 10 mM phosphate buffered saline at pH 7.7.

Another embodiment of the present invention relates to a nucleic acid formulation comprising a nucleic acid molecule, a pharmaceutically acceptable buffer to adjust the pH from about 7.0 to about 9.5, and triethanolamine or a pharmaceutically acceptable salt thereof. Triethanolamine may be added directly to the formulation as pure triethanolamine, which will form a salt in an aqueous solution. Triethanolamine may be added as a salt, the most common forms including but not being limited to the chloride, phosphate, bicarbonate, acetate, bromide, iodide, sulfate, succinate, citrate, malate and tartrate salts.

A further embodiment of the present invention relates to a nucleic acid formulation wherein the nucleic acid template is a plasmid DNA construct and which comprises a pharmaceutically acceptable buffer at a pH from about 7.0 to about 8.5, and triethanolamine or one of the pharmaceutically acceptable salts thereof.

The present invention also relates to a nucleic acid formulation wherein triethanolamine is a component of the formulation as well as a DNA plasmid template and a phosphate buffered saline wherein the pH is adjusted from about pH 7.0 to about pH 8.0 and the NaCl concentration is up to about 150 mM.

Another embodiment of the present invention relates to a nucleic acid formulation wherein triethanolamine is a component of the formulation as well as a DNA plasmid template and 10 mM phosphate buffered saline where the pH is adjusted to about 7.2.

A preferred embodiment of the present invention relates to a nucleic acid formulation wherein triethanolamine is present from about 0.1 mM to about 10 mM in 10 mM phosphate buffered saline at pH 7.2.

An especially preferred embodiment of the present invention relates to a nucleic acid formulation wherein the DNA plasmid of interest is present at 1.2 mM triethanolamine and 10 mM phosphate buffered saline, pH 7.2.

The present invention also relates to a nucleic acid pharmaceutical formulation which comprises both citrate and triethanolamine at respective concentrations which results in an increase in stability of the nucleic acid entity. This portion of the present invention relates to a nucleic acid formulation comprising a nucleic acid molecule, a pharmaceutically acceptable buffer to adjust the pH preferably from about 7.0 to about 9.5, citrate or a pharmaceutically acceptable citrate salt thereof as well as triethanolamine or an acceptable salt thereof.

A specific embodiment of the present invention relates to a nucleic acid formulation wherein citrate or a pharmaceutically acceptable salt thereof is present in a concentration from about 1 mM to about 20 mM and triethanolamine or a pharmaceutically acceptable salt thereof is present in a concentration from about 0.1 mM to about 2.0 mM, in addition to a DNA plasmid template in phosphate buffered saline from about 100 mM to about 200 mM NaCl, within a biologically effective pH, preferably between about 7.0 and 8.0.

A specific embodiment of the present invention relates to a nucleic acid formulation wherein citrate or a pharmaceutically acceptable salt thereof is present in a concentration from about 1 mM to about 20 mM and triethanolamine or a pharmaceutically acceptable salt thereof is present in a concentration from about 0.1 mM to about 2.0 mM, in addition to a DNA plasmid template in phosphate buffered saline at about 150 mM NaCl.

Another specific embodiment of the present invention relates to a nucleic acid formulation wherein citrate or a pharmaceutically acceptable salt thereof is present in a concentration from about 10 mM and triethanolamine or a pharmaceutically acceptable salt thereof is present in a concentration from about 0.1 mM to about 2.0 mM, in addition to a DNA plasmid template in phosphate buffered saline at about 150 mM NaCl.

A preferred embodiment of the present invention relates to a nucleic acid formulation which comprises the DNA plasmid of interest, citrate or a pharmaceutically acceptable salt at a concentration of 10 mM, triethanolamine or a pharmaceutically acceptable salt thereof is present in a concentration from about 0.1 mM to about 1.0 mM, in a phosphate buffered saline with about 100 mM to about 200 mM NaCl, within a biologically effective pH, preferably between about 7.0 and 8.0.

A preferred embodiment of the present invention relates to a nucleic acid formulation wherein citrate or a pharmaceutically acceptable salt thereof is present in a concentration from about 10 mM and triethanolamine or a pharmaceutically acceptable salt thereof is present in a concentration from about 0.1 mM to about 1.0 mM, in addition to a DNA plasmid template in phosphate buffered saline with about 150 mM NaCl.

An object of the present invention relates to a nucleic acid formulation for use in vaccine or gene therapy applications wherein DNA stability of the formulation is enhanced by the addition of citrate or a pharmaceutically acceptable salt thereof.

Another object of the present invention relates to a nucleic acid formulation for use in vaccine or gene therapy applications wherein DNA stability of the formulation is enhanced by the addition of triethanolamine or a pharmaceutically acceptable salt thereof.

A further object of the present invention relates to a nucleic acid formulation for use in vaccine or gene therapy applications wherein DNA stability of the formulation is enhanced by the addition of citrate and triethanolamine or a respective pharmaceutically acceptable salt thereof.

DETAILED DESCRIPTION OF THE INVENTION

Figure 1:
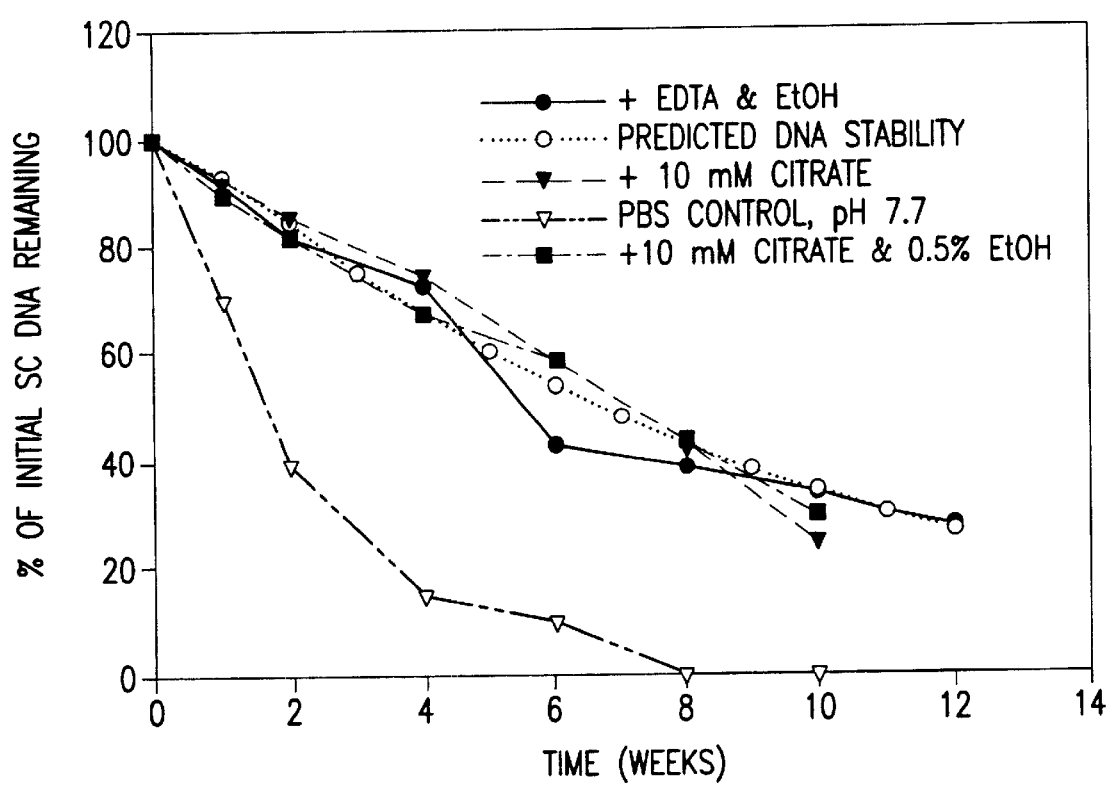
FIG. 1 shows the effect of citrate on DNA stability at pH 7.7 in 10 mM phosphate/150 mM NaCl, 50° C. (●)+EDTA, +ethanol; (○) predicted DNA stability; (▼)+10 mM citrate; (▽) PBS control; (■)+citrate, +ethanol.

To maximize DNA stability in a pharmaceutical formulation, the type of buffer, salt concentration, pH, light exposure as well as the type of sterilization process used to prepare the vials are all important parameters that must be controlled in the formulation to further optimize the stability. Furthermore, lyophilization of the DNA vaccine with appropriate formulation excipients can also be performed to enhance DNA stability, presumably by reducing molecular motion via dehydration. The present invention shows that the addition of citrate and/or triethanolamine increases the stability of such nucleic acid formulations.

During storage as a pharmaceutical entity, DNA plasmid vaccines undergo a physiochemical change in which the supercoiled plasmid converts to the open circular and linear form. A variety of storage conditions (low pH, high temperature, low ionic strength) can accelerate this process. The removal and/or chelation of trace metal ions from the DNA plasmid solution, the formulation itself and the vials and closures can stabilize the DNA plasmid from degradation during storage. In addition, non-reducing free radical scavengers are required to prevent damage of the DNA plasmid from free radical production that may still occur, even in apparently demetalated solutions. Furthermore, the buffer type, pH, salt concentration, light exposure, as well as the type of sterilization process used to prepare the vials, all must be controlled in the formulation to optimize the stability of the DNA vaccine. Lyophilization of the DNA vaccine in the presence of the appropriate formulation excipients can also be performed to stabilize the plasmid during storage. In the present invention, the addition of either citrate, triethanolamine or a combination of both citrate and triethanolamine has resulted in an increase in DNA stability on par with EDTA/ethanol based pharmaceutical formulations described in the art.

Therefore, the present invention relates to DNA pharmaceutical formulations which comprise citrate or a physiologically acceptable salt thereof at a concentration of about 100 mM in the absence of NaCl, or preferably in a range from about 1 mM to about 20 mM in the presence of about 150 mM NaCl, with an especially preferred citrate concentration of 10 mM. It will be within the purview of the artisan to utilize a citrate-containing formulation which comprises a physiologically acceptable buffer within a pH range which is acceptable for storage of a nucleic acid template, preferably in a pH range from about pH 7.0 to about pH 9.5; a salt (including but not limited to NaCl, KCl or LiCl) in the range of up to about 300 mM; and the highest appropriate DNA concentration in a sterile glass vial, packaged to protect the highly purified, nuclease free DNA from light. The physiologically acceptable buffers for use in the formulations of the present invention include but are not limited to Tris, glycine, sodium phosphate, potassium phosphate, lithium phosphate, sodium bicarbonate, potassium bicarbonate, lithium bicarbonate, sodium borate, potassium borate, lithium borate and sodium, potassium or lithium citrate, addition of sugars including but not limited to 6-carbon polyhydric alcohols such as sorbitol, mannitol and dulcitol and/or disaccharides such as sucrose, lactose, maltose or trehalose, as well as various adjuvants, including but not limited to aluminum containing adjuvants, which may stimulate the intended in vivo application.

A first embodiment of the present invention relates to a nucleic acid formulation comprising a nucleic acid molecule, a pharmaceutically acceptable buffer to adjust the pH from about pH 7.0 to about pH 9.5, and citrate or a pharmaceutically acceptable salt thereof, including but not limited to sodium, potassium, lithium and triethanolamine.

Another embodiment of the present invention relates to a nucleic acid formulation wherein the nucleic acid template is a plasmid DNA construct and which comprises a pharmaceutically acceptable buffer at a pH from about 7.0 to about 9.5, and citrate or a pharmaceutically acceptable salt thereof, including but not limited to sodium, potassium, lithium and triethanolamine.

Another embodiment of the present invention relates to a nucleic acid formulation wherein the nucleic acid template is a plasmid DNA construct and which comprises a pharmaceutically acceptable buffer at a pH from about 7.7 to about 8.5, and citrate or a pharmaceutically acceptable salt thereof, including but not limited to sodium, potassium, lithium and triethanolamine.

An additional embodiment of the present invention relates to a nucleic acid formulation wherein citrate is a component of the formulation as well as a DNA plasmid template and phosphate buffered saline wherein the pH is adjusted from about pH 7.0 to about pH 8.0 and the NaCl concentration is present in a range from about 100 mM to about 200 mM.

Yet another embodiment of the present invention relates to a nucleic acid formulation wherein citrate is a component of the formulation as well as a DNA plasmid template and 10 mM phosphate buffered saline at pH 7.7.

A preferred embodiment of the present invention relates to a nucleic acid formulation wherein citrate is present at about 100 mM in 10 mM phosphate buffer or is present from about 1 mM to about 20 mM in 10 mM phosphate buffered saline at pH 7.7.

An especially preferred embodiment of the present invention relates to a nucleic acid formulation wherein the DNA plasmid of interest is present in 10 mM citrate and 10 mM phosphate buffered saline at pH 7.7.

The present invention is also related to pharmaceutical formulations which comprise triethanolamine or a pharmaceutically acceptable salt thereof at a concentration range from about 0.1 mM to about 10 mM, preferably in a range from about 0.1 mM to about 2.0 mM, with an especially preferred range being from about 1.0 mM triethanolamine to about 2.0 mM triethanolamine. As noted above for citrate-containing solutions, it will be within the purview of the artisan to utilize a triethanolamine-based formulation which comprises a pharmaceutically acceptable buffer within a pH range which promotes stability of the nucleic acid template, preferably a pH range from about 7.0 to about 9.5; a salt (including but not limited to NaCl, KCl or LiCl) in the range of up to about 300 mM, and the highest appropriate DNA concentration in a sterile glass vial, packaged to protect the highly purified, nuclease free DNA from light. The pharmaceutically acceptable buffers for use in the formulations of the present invention include but are not limited to Tris, glycine, sodium phosphate, potassium phosphate, lithium phosphate, sodium bicarbonate, potassium bicarbonate, lithium bicarbonate, sodium borate, potassium borate, lithium borate and sodium, potassium or lithium citrate, addition of sugars including but not limited to 6-carbon polyhydric alcohols such as sorbitol, mannitol and dulcitol and/or disaccharides such as sucrose, lactose, maltose or trehalose, as well as various adjuvants, including but not limited to aluminum containing adjuvants, which may stimulate the intended in vivo application.

Another embodiment of the present invention relates to a nucleic acid formulation comprising a nucleic acid molecule, a pharmaceutically active buffer to adjust the pH from about 7.0 to about 8.5, and triethanolamine or a pharmaceutically acceptable salt thereof. Triethanolamine may be added directly to the formulation as pure triethanolamine, which will form a salt in an aqueous solution. Triethanolamine may also be added as a salt, the most common forms including but not being limited to the chloride, phosphate, bicarbonate, acetate, bromide, iodide, sulfate, succinate, citrate, malate and tartrate salts.

A further embodiment of the present invention relates to a nucleic acid formulation wherein the nucleic acid template is a plasmid DNA construct and which comprises a pharmaceutically acceptable buffer at a pH from about 7.0 to about 8.0, and triethanolamine or a pharmaceutically acceptable salt thereof.

The present invention also relates to a nucleic acid formulation wherein triethanolamine is a component of the formulation as well as a DNA plasmid template and a phosphate buffered saline wherein the pH is adjusted from about pH 7.0 to about pH 8.0 and the NaCl concentration is from about 100 mM to about 200 mM.

Another embodiment of the present invention relates to a nucleic acid formulation wherein triethanolamine is a component of the formulation as well as a DNA plasmid template and 10 mM phosphate buffered saline where the pH is adjusted to about 7.2.

A preferred embodiment of the present invention relates to a nucleic acid formulation wherein triethanolamine is present from about 0.1 mM to about 2.0 mM in 10 mM phosphate buffered saline, pH7.2.

An especially preferred embodiment of the present invention relates to a nucleic acid formulation wherein the DNA plasmid of interest is present in 1.2 mM triethanolamine in 10 mM phosphate buffered saline, pH 7.2.

The present invention also relates to a nucleic acid pharmaceutical formulation which comprises both citrate and triethanolamine at respective concentrations which results in an increase in stability of the nucleic acid entity. The skilled artisan may use the teachings of this specification to generate various nucleic acid formulations which contain citrate and triethanolamine which result in increased nucleic acid stability. To this end, variations in formulation composition may include, but are not limited to, variations in pH through a biologically active range, preferably a range from about 7.0 to about 9.5; variations in the buffers utilized, including but not limited to Tris, glycine, sodium phosphate, potassium phosphate, lithium phosphate, sodium bicarbonate, potassium bicarbonate, lithium bicarbonate, sodium borate, potassium borate, lithium borate and sodium, potassium or lithium citrate; variations in salt concentration, and addition of sugars including but not limited to 6-carbon polyhydric alcohols such as sorbitol, mannitol and dulcitol and/or disaccharides such as sucrose, lactose, maltose or trehalose, as well as various adjuvants which may stimulate the intended in vivo application. It will be evident to one of ordinary skill in the art that a formulation of this portion of the present invention will have a tonicity that is acceptable for parenteral injection.

One embodiment of this portion of the present invention relates to a nucleic acid formulation comprising a nucleic acid molecule, a pharmaceutically acceptable buffer to adjust the pH from about 7.0 to about 9.5, citrate or a pharmaceutically acceptable citrate salt thereof (including but not limited sodium, potassium, lithium and triethanolamine salts) as well as triethanolamine or an acceptable salt thereof. As noted above, triethanolamine may be added directly to an aqueous formulation as pure triethanolamine to form a salt, or in turn, may be added as a triethanolamine salt, including but not limited to the chloride, phosphate, bicarbonate, acetate, bromide, iodide, sulfate, succinate, citrate, malate and tartrate salts. Therefore, one embodiment of the present invention relates to a nucleic acid formulation wherein the nucleic acid template is a plasmid DNA construct and wherein the formulation further comprises a pharmaceutically acceptable buffer at a biologically acceptable pH, including but not limited to a range from about 7.0 to about 9.5, as well as citrate or a pharmaceutically acceptable citrate salt in addition to triethanolamine or a pharmaceutically acceptable triethanolamine salt.

A further embodiment of the present invention relates to a nucleic acid formulation wherein citrate and triethanolamine, or their respective salts, are a component of the formulation as well as a DNA plasmid template and phosphate buffered saline wherein the NaCl concentration is present in a range from about 100 mM to about 200 mM, within a biologically effective pH, preferably between about 7.0 and 8.0.

A specific embodiment of the present invention relates to a nucleic acid formulation wherein citrate or a pharmaceutically acceptable salt thereof is present in a concentration from about 1 mM to about 20 mM and triethanolamine or a pharmaceutically acceptable salt thereof is present in a concentration from about 0.1 mM to about 2.0 mM, in addition to a DNA plasmid template in phosphate buffered saline from about 100 mM to about 200 mM NaCl, within a biologically effective pH, preferably between about 7.0 and 8.0.

A specific embodiment of the present invention relates to a nucleic acid formulation wherein citrate or a pharmaceutically acceptable salt thereof is present in a concentration from about 1 mM to about 20 mM and triethanolamine or a pharmaceutically acceptable salt thereof is present in a concentration from about 0.1 mM to about 2.0 mM, in addition to a DNA plasmid template in phosphate buffered saline at about 150 mM NaCl.

Another specific embodiment of the present invention relates to a nucleic acid formulation wherein citrate or a pharmaceutically acceptable salt thereof is present in a concentration from about 5 mM to about 10 mM and triethanolamine or a pharmaceutically acceptable salt thereof is present in a concentration from about 0.1 mM to about 2.0 mM, in addition to a DNA plasmid template in phosphate buffered saline at about 150 mM NaCl.

A preferred embodiment of the present invention relates to a nucleic acid formulation which comprises the DNA plasmid of interest, citrate or a pharmaceutically acceptable salt at a concentration of about 5 mM to about 10 mM, triethanolamine or a pharmaceutically acceptable salt thereof is present in a concentration from about 0.1 mM to about 1.0 mM, in a phosphate buffered saline with about 100 mM to about 200 mM NaCl, within a biologically effective pH, preferably between about 7.0 and 8.0.

A preferred embodiment of the present invention relates to a nucleic acid formulation wherein citrate or a pharmaceutically acceptable salt thereof is present in a concentration from about 5 mM and triethanolamine or a pharmaceutically acceptable salt thereof is present in a concentration from about 0.1 mM to about 1.0 mM, in addition to a DNA plasmid template in phosphate buffered saline with about 150 mM NaCl.

Another preferred embodiment of the present invention relates to a nucleic acid formulation wherein citrate or a pharmaceutically acceptable salt thereof is present in a concentration from about 5 mM and triethanolamine or a pharmaceutically acceptable salt thereof is present in a concentration from about 0.1 mM to about 0.5 mM, in addition to a DNA plasmid template in phosphate buffered saline with about 150 mM NaCl.

The standard techniques of molecular biology for preparing and purifying DNA constructs enable the preparation of the DNA therapeutics of this invention. The amount of expressible DNA to be introduced to a vaccine recipient will depend on the strength of the transcriptional and translational promoters used in the DNA construct, and on the immunogenicity of the expressed gene product. In general, an immunologically or prophylactically effective dose of about 1 µg to 10 mg, and preferably about 1 mg to 5 mg is administered directly into muscle tissue. Subcutaneous injection, intradermal introduction, impression through the skin, and other modes of administration such as intraperitoneal, intravenous, or inhalation delivery are also contemplated. It is also contemplated that booster vaccinations are to be provided.

The DNA may be naked, that is, unassociated with any proteins, adjuvants or other agents which impact on the recipients immune system. In this case, it is desirable for the DNA to be in a physiologically acceptable solution, such as, but not limited to, sterile saline or sterile buffered saline. Alternatively, the DNA may be associated with liposomes, such as lecithin liposomes or other liposomes known in the art, as a DNA-liposome mixture, (see for example WO93/24640) or the DNA may be associated with an adjuvant known in the art to boost immune responses, such as a protein or other adjuvants known in the art, including but not limited to aluminum-containing adjuvants. Agents which assist in the cellular uptake of DNA, such as, but not limited to, calcium ions, viral proteins and other transfection facilitating agents may also be used to advantage. These agents are generally referred to as transfection facilitating agents and as pharmaceutically acceptable carriers. As used herein, the term gene refers to a segment of nucleic acid which encodes a discrete polypeptide. The terms construct, and plasmid are used interchangeably. The term vector is used to indicate a DNA into which genes may be cloned for use according to the method of this invention.

EXAMPLE 1

DNA Purification

Multi-Gram Scale Purification of Plasmid DNA—4.5 L of frozen E. coli cell slurry was used to make 33.7 L of cell suspension in STET buffer (8% sucrose, 2% Triton, 50 mM Tris buffer, 50 mM EDTA, pH 8.5) with 2500 units/ml of lysozyme. The absorbance of the suspension at 600 nm was about O.D. 30. The suspension was stirred at room temperature for 15 minutes to ensure proper mixing and then was incubated for 45 minutes with continuous stirring at 37° C. Following incubation, mixing was continued at room temperature and the cell suspension was pumped through the heat exchanger at a flow rate of 500 ml/min. The batch temperature was maintained at 100° C. and the inlet and outlet temperatures of the cell suspension were measured to be about 24° C. and between 70–77° C., respectively. The cell lysate exiting the heat exchanger was collected in Beckman centrifuge bottles (500 mls each) and the material was centrifuged immediately in Beckman J-21 centrifuges for 50 minutes at 9000 RPM. Following centrifugation, the supernatant was found to contain 4–5 times more plasmid product than in the case without lysozyme incubation. The supernatant product of the centrifugation was immediately diafiltered against 3 volumes of TE 35 buffer (25 mM Tris-EDTA at pH 8.0) and then incubated with $20 \times 10^5$ units of E. coli RNase for 2–4 hours at room temperature. After completion of the incubation, the product solution was then diafiltered an additional 6 volumes with TE buffer using a 100 kD MWCO membrane and then filtered through a 0.45 micron filter to remove residual debris. The filtered lysate was diluted to 0.7 M NaCl with a 20 mM Bis/Tris Propane-NaCl buffer at pH 7.5, which prepares the diluted filtrate for loading onto the anion exchange column. The anion exchange column (3.6 L of POROS PI/M) was previously equilibrated with 20 mM Bis/Tris Propane and 0.7M NaCl. The filtered lysate was loaded to column capacity. In this case 5 grams of supercoiled plasmid was loaded onto the anion exchange column. After loading, the column was washed with 2–4 column volumes of 20 mM Bis/Tris Propane and 0.7 M NaCl. A 10 column volume gradient from 0.7 M NaCl to 2.0 M NaCl in 20 mM Bis/Tris Propane was performed to clear most of the E. coli protein, RNA and some endotoxin. The supercoiled plasmid fraction eluted between 1.4 M and 2.0 M NaCl. The supercoiled fraction from the anion exchange column, which contained 4 grams of supercoiled plasmid was then diluted 2–3 times with pyrogen free water, adjusted to 1.2% IPA and pH adjusted to 8.5 with 1 N NaOH. The diluted anion exchange supercoiled fraction was then loaded onto a 7 L reversed phase column (POROS R2/M) which had been previously equilibrated with 100 mM Ammonium Bicarbonate containing 1.2% IPA. In this case, 3.2 grams of supercoiled plasmid were loaded onto the reversed phase column and then the column was washed with 6–10 column volumes of 1.2% IPA in 100 mM Ammonium Bicarbonate. This extensive wash was performed to clear impurities. Next, a gradient of 1.2% IPA to 11.2% IPA in 5 column volumes was performed. The supercoiled plasmid fraction elutes at about 4% IPA. The supercoiled product fraction from the reversed phase column was then concentrated and diafiltered into normal saline using a 30 kD MWCO membrane. The final product bulk was filtered through a 0.22 micron filter. The overall product yield of the process was more than 50% of the supercoiled plasmid in the clarified cell lysate as indicated by the anion exchange HPLC assay.

EXAMPLE 2

Effect of Citrate on DNA Stability at pH 7.2 and 7.7

Kinetics of DNA Degradation During Storage— Experimental conditions were as follows: Plasmid DNA (FR-9502 HA-Georgia) was diluted into a formulation buffer to a final concentration of 20 µg/mL. To determine the stability of the DNA, 0.8 mL of each DNA formulation was placed in a 3 mL glass vial and capped with a Teflon coated stopper. After various periods of incubation in an inverted position at 50° C., individual vials were removed from the incubator and the DNA containing solution was analyzed by agarose gel electrophoresis to determine the percentage of supercoiled, open circle and linear DNA forms. The stability data below refer to the percent of initial supercoiled (SC) DNA remaining after the indicated period of incubation.

Enhancement of DNA stability by citrate—PCT International publication WO97/40839 discloses the importance of trace metal ions on DNA stability. Moreover, the data shows that combinations of metal ion chelators and free radical scavengers other than EDTA and ethanol might be effective stabilizers of DNA. Citrate was tested as a potential stability enhancer due to its capacity to bind trace metal ions and was tested with and without the presence of ethanol at pH 7.2 and pH 8.0, since EDTA/ethanol combinations are more effective at pH 8.0 than at 7.2. The results in FIG. 1 show that the addition of 10 mM citrate to a formulation containing 10 mM phosphate, 150 mM NaCl at pH 7.7 increased the stability of the DNA to a comparable level as a combination of 100 $\mu$M EDTA and 0.5% ethanol. Moreover, the stability of the DNA in the citrate formulation, after 6 weeks at 50° C., was equivalent to that predicted in the absence of free radical oxidation at pH 7.7, 50° C. These results show that citrate is a potent inhibitor of free radical oxidation at pH 7.7. The data in FIG. 1 also show that the stability of plasmid DNA in formulations containing both citrate and ethanol was the same as that of the DNA in the formulation containing citrate alone. Therefore, the results indicate that citrate does not enhance DNA stability solely by acting as a metal ion chelator, as EDTA does, and as expected. Instead, or in addition to its ability to bind trace metal ions, citrate inhibited the free radical oxidation of the DNA. In contrast, EDTA was found to decrease DNA stability in the absence of ethanol (see WO 97/40839).

Figure 2:
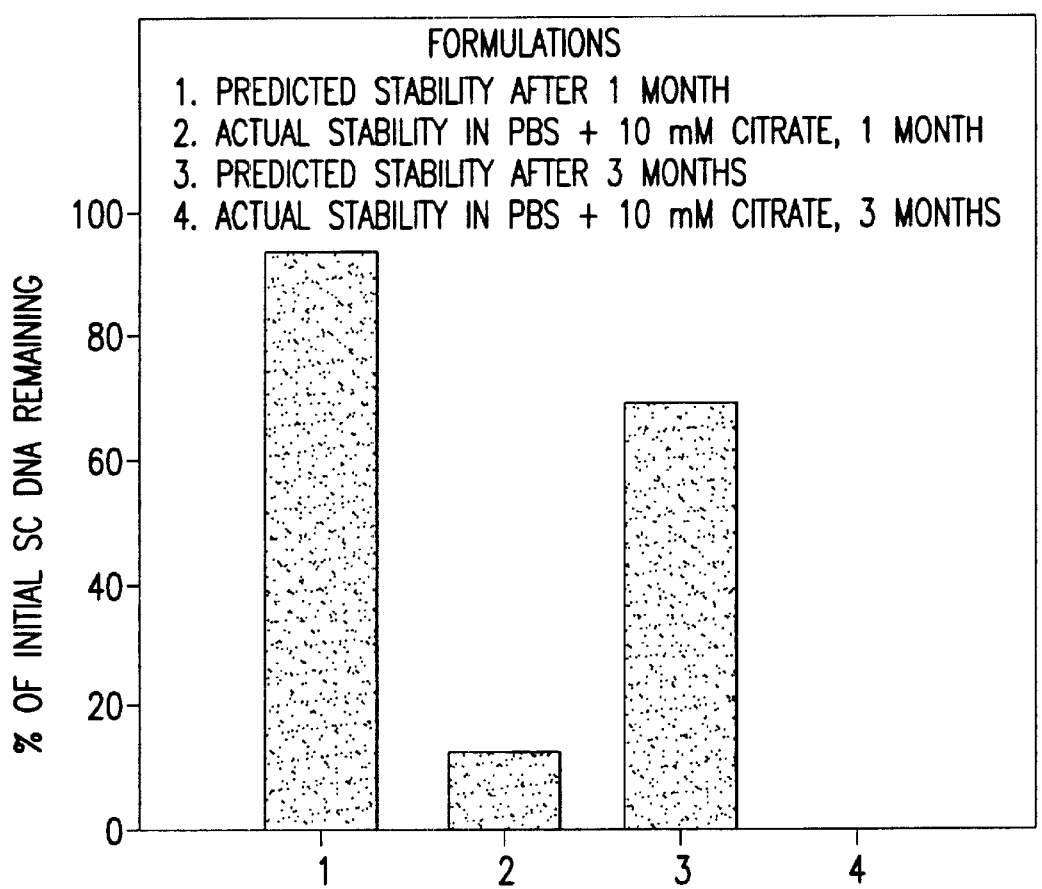
FIG. 2 shows the stability of plasmid DNA in formulations containing citrate vs. predicted stability in the absence of free radical oxidation at pH 7.2, 37° C. (1) is predicted stability after 1 month, (2) is actual stability in PBS, 10 mM citrate after 1 month, (3) is predicted stability after 3 months, (4) is actual stability in PBS, 10 mM citrate after 3 months.
Figure 3:
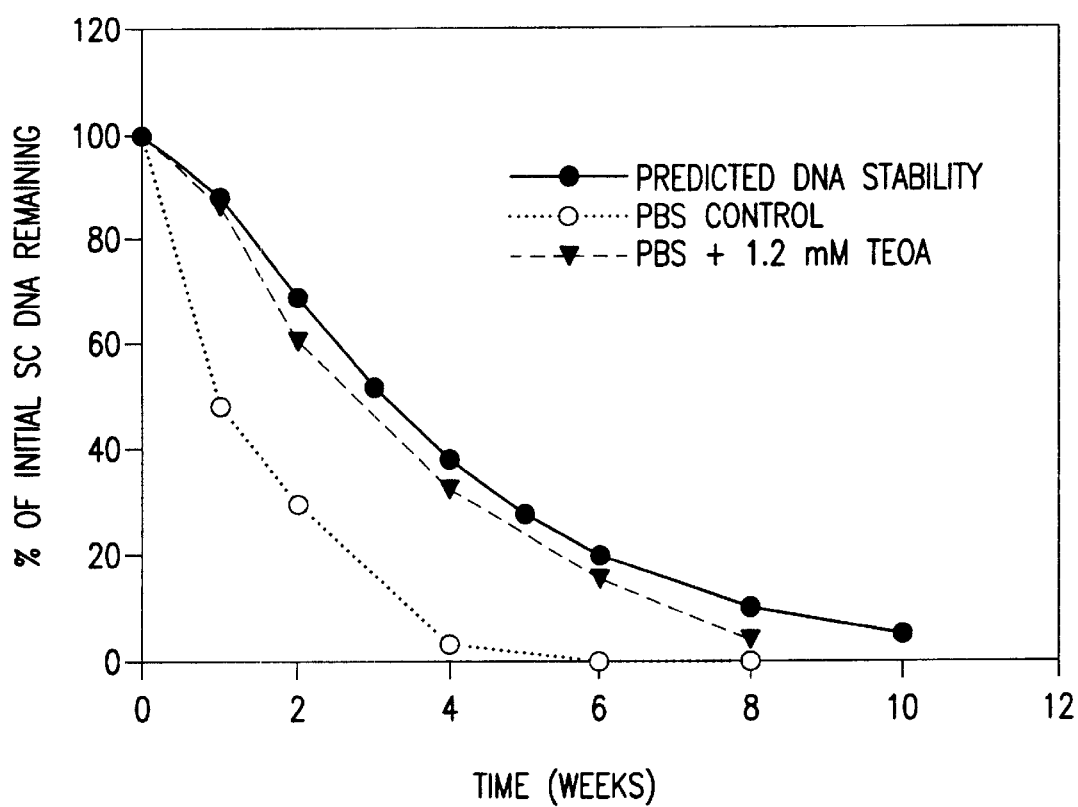
FIG. 3 shows the effect of triethanolamine on DNA stability at pH 7.2, in PBS at 50° C. (●) predicted DNA stability; (○)+1.2 mM triethanolamine; (▼) PBS control.

The predictions of DNA stability in FIGS. 1–3 were made using the equations derived in PCT application WO 97/40839. The rate constants for depurination and $\beta$-elimination that were used to make these predictions were experimentally determined by measuring the change in supercoiled DNA content in samples containing plasmid DNA at 100 mcg/mL in a solution that is believed to completely inhibit free radical oxidation of the DNA (10 mM phosphate, 150 mM NaCl, 0.5 mM EDTA, 1% ethanol, pH 7.4). The depurination and $\beta$-elimination rate constants at pH 7.2, 37° C. were determined to be $1.4\times10^{-11}$ s$^{-1}$ and $1.7\times10^{-7}$ s$^{-1}$, respectively. The depurination and $\beta$-elimination rate constants at pH 7.2, 50° C. were determined to be $8.9\times10^{-11}$ s$^{-1}$ and $8.8\times10^{-7}$ s$^{-1}$, respectively. The depurination and $\beta$-elimination rate constants at pH 7.7, 50° C. were determined to be $2.8\times10^{-11}$ s$^{-1}$ and $2.8\times10^{-6}$ s$^{-1}$, respectively.

FIG. 2 shows the stability of DNA in formulations containing citrate compared to the predicted stability of the DNA in the absence of free radical oxidation, at pH 7.2, 37° C. The results indicate that citrate does not enhance the stability of the DNA to the level predicted in the absence of free radical oxidation at pH 7.2. Therefore, pH influences the ability of citrate to stabilize DNA.

EXAMPLE 3

Effect of Triethanolamine on DNA Stability

Enhancement of DNA stability by citrate—The plasmid DNA template was as described in Example Section 2. The effect of 1.2 mM triethanolamine (TEOA) on DNA stability at 50° C. is shown in FIG. 3. The results indicate that the stability of the DNA in a TEOA-containing formulation was nearly equivalent to that predicted in the absence of free radical oxidation at 50° C., pH 7.2. These results show that triethanolamine is an effective scavenger of free radicals at pH 7.2.

EXAMPLE 4

Effects of Citrate and Triethanolamine on the Stability of Supercoiled (SC) Plasmid DNA The stability of plasmid DNA was evaluated in several formulations at 50° C. to establish the optimum concentrations of citrate and triethanolamine for enhancing DNA stability. Each formulation contained 0.8 mL of 20 mg/mL plasmid DNA (initially ~95% SC) filled in 3 mL molded glass vials equipped with Teflon coated stoppers. Stability was assessed by agarose gel electrophoresis followed by ethidium bromide staining. Formulations having higher DNA stability were defined as those that maintained higher percent supercoiled DNA over time or those that had the lowest accumulation of linear DNA. The formulation buffer for formulations A1-A12 contained 6 mM sodium phosphate and 150 mM NaCl at pH 7.2 while the buffer for formulations B1-B12 contained 10 mM sodium phosphate and 150 mM NaCl at pH 8.0. The additional excipients added to the formulations are indicated below.

| Formulation | Description |
|---|---|
| A/B-1 | buffer control |
| A/B-2 | + 0.1 mM triethanolamine |
| A/B-3 | + 0.5 mM triethanolamine |
| A/B-4 | + 1.0 mM triethanolamine |
| A/B-5 | + 5.0 mM triethanolamine |
| A/B-6 | + 1.0 mM citrate |
| A/B-7 | + 5.0 mM citrate |
| A/B-8 | + 10 mM citrate |
| A/B-9 | + 0.1 mM triethanolamine and 5.0 mM citrate |
| A/B-10 | + 0.1 mM triethanolamine and 1.0 mM citrate |
| A/B-11 | + 0.5 mM triethanolamine and 5.0 mM citrate |
| A/B-12 | + 100 $\mu$M EDTA and 0.5% Ethanol |

The percent of initial supercoiled DNA remaining after 4 weeks at 50° C. and the percent linear DNA after 14 weeks at 50° C. are shown in Table 1. Based on the analysis of SC DNA remaining both citrate and triethanolamine significantly enhanced plasmid DNA stability. The results also indicate that citrate was more effective at enhancing DNA stability than triethanolamine but required higher concentrations. Combinations of citrate and triethanolamine were not more effective than 10 mM citrate alone. Citrate at 10 mM (A-8) was also more effective than the combination of EDTA and ethanol (A-12) at this pH. The optimum concentration of triethanolamine was 0.5 mM while the highest concentration of citrate used (10 mM) provided the highest stability.

TABLE 1

Stability of plasmid DNA at pH 7.2.

| Formulation | % SC DNA* | % linear DNA** |
|---|---|---|
| A-1 | 5 | 35 |
| A-2 | 9 | 21 |
| A-3 | 18 | 19 |

TABLE 1-continued

Stability of plasmid DNA at pH 7.2.

| Formulation | % SC DNA* | % linear DNA** |
|---|---|---|
| A-4 | 14 | 18 |
| A-5 | 10 | 26 |
| A-6 | 11 | 20 |
| A-7 | 24 | 10 |
| A-8 | 32 | 11 |
| A-9 | 29 | 6 |
| A-10 | 26 | 20 |
| A-11 | 18 | 10 |
| A-12 | 22 | 7 |

*% of initial supercoiled DNA remaining after 4 weeks
**% linear DNA after 14 weeks at 50° C.

The conclusions based on the analysis of linear DNA after 14 weeks at 50° C. are similar to those based on the analysis of SC DNA, with two exceptions. The results indicated that the combination of 0.1 mM triethanolamine and 5 mM citrate (A-9) was more effective than either citrate or triethanolamine alone. Moreover, the results indicated that 10 mM citrate (A-8) was not more effective than the combination of EDTA and ethanol (A-12). Formulations A-9 and A-12 provided the highest DNA stability.

The stability of plasmid DNA at pH 8.0 was evaluated by measuring both the percent SC DNA remaining and the percent linear DNA after 14 weeks at 50° C. The results, shown in Table 2, clearly indicate that both citrate and triethanolamine significantly enhanced DNA stability. However, the results were slightly different than those at pH 7.2. The most significant difference was that triethanolamine enhanced DNA stability as effectively as citrate at this pH. The results also indicated that the formulation containing 0.5 mM triethanolamine and 5 mM citrate (B-11) was more effective than either triethanolamine or citrate alone, and was nearly as effective as the combination of EDTA and ethanol (B-12). Taken together these results indicate that citrate and triethanolamine are effective enhancers of DNA stability and that under certain conditions the combination of citrate and triethanolamine provided higher DNA stability than the use of either substance alone.

TABLE 2

Stability of plasmid DNA at pH 8.0.

| Formulation | % SC DNA* | % linear DNA** |
|---|---|---|
| B-1 | 0 | 48 |
| B-2 | 6 | 10 |
| B-3 | 11 | 6 |
| B-4 | 10 | 6 |
| B-5 | 3 | 7 |
| B-6 | 0 | 27 |
| B-7 | 7 | 9 |
| B-8 | 10 | 7 |
| B-9 | 16 | 2 |
| B-10 | 5 | 6 |
| B-11 | 17 | 1 |
| B-12 | 23 | 1 |

*% of initial supercoiled DNA remaining after 14 weeks
**% linear DNA after 14 weeks at 50° C.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed:

1. A nucleic acid formulation comprising:
    a) a nucleic acid molecule;
    b) an amount of a pharmaceutically acceptable buffer to adjust the pH from about 7.0 to about 9.5;
    c) a salt at concentration from about 100 mM to about 300 mM; and,
    d) citrate or a pharmaceutically acceptable salt thereof at a concentration less than 15 mM.

2. The nucleic acid formulation of claim 1 wherein the pharmaceutically acceptable buffer is a phosphate buffered saline wherein the pH is from about pH 7.0 to about pH 8.0 and the salt is NaCl at a concentration from about 100 mM to about 200 mM.

3. The nucleic acid formulation of claim 2 wherein the citrate or a pharmaceutically acceptable salt thereof is present at a concentration of about 10 mM.

4. The nucleic acid formulation of claim 3 wherein the NaCl concentration is about 150 mM.

5. The nucleic acid formulation of claims 1, 2, 3 or 4 wherein the nucleic acid molecule is a DNA plasmid molecule.

6. A DNA plasmid formulation comprising:
    a) a DNA plasmid molecule;
    b) an amount of a pharmaceutically acceptable buffer to adjust the pH from about 7.0 to about 9.5;
    c) a salt at concentration of up to about 300 mM; and
    d) triethanolamine or a pharmaceutically acceptable salt thereof at a concentration of about 0.1 mM to about 10 mM,
wherein the DNA plasmid formulation is free of carrier molecules.

7. The DNA plasmid formulation of claim 6 wherein the pharmaceutically acceptable buffer is a phosphate buffered saline wherein the pH is from about pH 7.0 to about pH 8.0 and the salt is NaCl at a concentration from about 100 mM to about 200 mM.

8. The DNA plasmid formulation of claim 7 wherein the buffer is 10 mM phosphate containing 150 mM NaCl.

9. The DNA plasmid formulation of claim 8 wherein the pH is about 7.2.

10. The DNA plasmid formulation of claim 9 wherein the triethanolamine or a pharmaceutically acceptable salt thereof is present in a concentration of about 0.1 mM to about 10 mM.

11. The DNA plasmid formulation of claim 10 wherein the triethanolamine or a pharmaceutically acceptable salt thereof is present in a concentration from about 0.1 mM to about 2.0 mM.

12. The nucleic acid formulation comprising:
    a) a nucleic acid molecule;
    b) an amount of a pharmaceutically acceptable buffer to adjust the pH from about 7.0 to about 9.5;
    c) a salt at a concentration of up to about 300 mM;
    d) citrate or a pharmaceutically acceptable salt; and,
    e) triethanolamine or a pharmaceutically acceptable salt thereof,
wherein the nucleic acid formulation is free of carrier molecules.

13. The nucleic acid formulation of claim 12 wherein the pharmaceutically acceptable buffer is phosphate buffered saline and the salt is NaCl at a concentration from about 100 mM to about 200 mM.

14. The nucleic acid formation of claim 13 wherein the citrate concentration is about 5 mM.

15. The nucleic acid formulation of claim 14 wherein the triethanolamine concentration is present from about 0.1 mM to about 2.0 mM.

16. The nucleic acid formulation of claim 15 wherein the NaCl is at a concentration of about 150 mM.

17. The nucleic acid formulation of claim 13 wherein the citrate concentration is from about 1 mM to about 20 mM.

18. The nucleic acid formulation of claim 17 wherein the triethanolamine concentration is from about 0.1 mM to about 2.0 mM.

19. The nucleic acid formulation of claim 18 wherein the NaCl is at a concentration of about 150 mM.

20. The nucleic acid formulation of claims 12, 13, 17, 18, 19, 14, 15 or 16 wherein the nucleic acid molecule is a DNA plasmid molecule.

* * * * *